United States Patent [19]

Beierle et al.

[11] 4,291,017

[45] Sep. 22, 1981

[54] METHOD FOR LIMITING ADHERENCE OF PLAQUE AND DENTAL COMPOSITION THEREFOR

[75] Inventors: John W. Beierle, San Marino; Dale E. Grenoble, Malibu, both of Calif.

[73] Assignee: Dental Concepts, Inc., Santa Monica, Calif.

[21] Appl. No.: 95,699

[22] Filed: Nov. 19, 1979

[51] Int. Cl.³ .................................................. A61K 7/18
[52] U.S. Cl. ..................................... 424/52; 128/24 A; 433/119; 433/216; 424/151
[58] Field of Search ........................... 424/49, 52, 151

[56] References Cited

U.S. PATENT DOCUMENTS

| | | | |
|---|---|---|---|
| 3,531,564 | 9/1970 | Bouchal et al. | 424/52 |
| 3,591,675 | 7/1971 | Brilliant | 424/54 |
| 3,751,568 | 8/1973 | Mundorff et al. | 424/52 |
| 3,887,712 | 6/1975 | Lover et al. | 424/326 |
| 3,947,570 | 3/1976 | Pensak | 424/54 |
| 3,970,747 | 7/1976 | Barth | 424/52 |

OTHER PUBLICATIONS

Linke et al., Z. Naturforsch. C. Biosci., 1976, 31C (5-6): 245-251.
Linke, Z. Naturforsch. C. Biosci., 1977, 32C (9-10): 839-843.
Reed et al., J. Dent. Res. 55: 357-358, May-Jun., 1976.
Mundorf et al., J. Dent. Res. 51: 1567-1571, Nov.-Dec., 1972.
Bibby et al., J. Dent. Res. Special Issue 54: B137-B142, 1975.
Tinanoff, J. Dent. Res. 56 (Spec. Issue A), 1977, A138.
Wefel et al., J. Dent. Res. 56 (Spec. Issue B), 1977, B132.
Mundorf et al., J. Dent. Res. 56, Spec. Issue A, 1977, A109.

*Primary Examiner*—Shep K. Rose
*Attorney, Agent, or Firm*—Nilsson, Robbins, Dalgarn, Berliner, Carson & Wurst

[57] ABSTRACT

A dentrifice containing a limited amount, 0.001-0.05% by weight, of titanium tetrafluoride, and preferably at least 0.5% by weight xylitol or 0.01% by weight saccharin, is applied to a person's teeth to limit the adherence of plaque to the teeth. The method finds particular advantage when used as a liquid in conjunction with cavitation cleaning of the teeth.

11 Claims, No Drawings

METHOD FOR LIMITING ADHERENCE OF PLAQUE AND DENTAL COMPOSITION THEREFOR

BACKGROUND AND SUMMARY OF THE INVENTION

It has long been known that the usual means of cleaning teeth, such as by a toothbrush, does not adequately remove plaque. To properly clean the teeth requires proper use of dental floss along with brushing. However, it is also known that most people do not have the required manual dexterity or refuse to spend the amount of time necessary to properly clean teeth. To solve some of the problems related to the usual ineffective use of a toothbrush and toothpaste, such devices as vibrating toothbrushes, pulsating water apparatus and ultrasonic toothcleaning apparatus have been devised. Examples of ultrasonic devices which are particularly efficient are described in Application Ser. No. 790,312, filed Apr. 25, 1977 for "Ultrasonic Tooth Cleaner" by E. E. Hatter, R. H. Taylor and R. D. McGunigle issued as U.S. Pat. No. 4,176,454, and in Application Ser. No. 12,984, filed Feb. 21, 1979 by E. E. Hatter, R. H. Taylor and R. D. McGunigle issued as U.S. Pat. No. 4,236,510, the disclosures of said patent being incorporated herein by reference. Such devices are used in conjunction with a liquid serving as a medium for the transmission of sonic energy from the transducer of the device throughout the mouth cavity to the surfaces of the teeth. The devices operate by cavitating the liquid, which in turn serves to loosen plaque from the surfaces of the teeth.

Depending upon the extent of adherence of plaque to a patient's teeth, the level of power used by the ultrasonic cavitation device will be more or less effective in removing the plaque. Generally, lower power levels are more desirable in being safer and less damaging, instantaneously and accumulatively, to gum tissue. Accordingly, patients with more adherent plaque would take longer for the plaque to be removed. Up until now, there was little one could do to modify the effectiveness of the procedure with respect to any particular patient's mouth. In particular, the coupling liquid has served merely as a means for supporting the cavitation and did not take an active part in a program for plaque removal.

The present invention provides a dental composition which can be used as a liquid coupler for a cavitation device, serving not only the mechanical cavitation function but also providing a means for modifying the nature of the plaque in a patient's mouth. More particularly, the composition provided herewith when used on a daily maintenance basis can result in plaque which is not as adherent as plaque which would otherwise be formed.

The present invention therefore provides a method for reducing the cohesiveness of bacterial plaque and the adherence of plaque to teeth, and a dental composition therefor. Specifically, a method is provided for limiting the adherence to teeth of plaque comprising applying daily to a person's teeth a dentrifice containing a limited amount, 0.001–0.05% by weight, of titanium tetrafluoride, preferably in combination with at least 0.5% by weight xylitol, or 0.01% by weight saccharin.

When used in a maintenance program, the dentrifice can be in any of the usual forms for topical application, such as toothpastes, tooth powders, dental creams, chewing gums and the like, but it is advantageously in liquid form so as to be usable as a mouthwash and in the preferred form of the invention as a coupling liquid for a cavitation procedure. As will be described in more detail hereinafter, the particular formulation when used on a daily maintenance basis results in plaque which is not as adherent as plaque which would otherwise be formed, thereby enabling the use of a cavitation device of lower power than otherwise would be used, with a resultant greater margin of safety.

DETAILED DESCRIPTION

It is to be understood that dental compositions embodying the present invention may be used on a daily maintenance basis in any convenient form by the addition thereto of various solids and liquids customarily incorporated into dentrifices. Accordingly, the composition may be in the form of toothpastes, tooth powders, dental creams and even chewing gums and the like. However, for purposes of the present description, the composition will be described as a liquid which can be used as a coupling agent for the ultrasonic cleaning of teeth. In this regard, the liquid can also be used directly as a mouthwash before, during and/or after a cavitation procedure. The liquid composition is also efficaceous as a mouthwash for plaque control without the use of the cavitation device.

In a particular form of the invention, the dental composition comprises a dentrifice containing the following components in percentage by weight:

| | |
|---|---|
| Ethyl alcohol | 6–20% |
| Titanium tetrafluoride | 0.001–0.05% |
| Xylitol or saccharin | 0.5–10% (xylitol); 0.01–1.0% (saccharin) |
| NaCl | 0–4% |
| Surfactant | 0–1.0% |
| Flavoring agent | 0–5% |
| Coloring agent | 0–2% |
| Buffer | 0–1% |
| Antibacterial agent | 0–1% |
| Glycerin | 0–5% |
| Water | Q.S. |

The ethyl alcohol serves as a mild astringent of low surface tension, solubilizes other components and has some antibacterial properties.

The titanium tetrafluoride is a key ingredient of the dental composition and it is particularly important that it be provided in the limited amount indicated. The use of titanium tetrafluoride in much larger amounts, i.e., 1% by weight or more, is known to have anti-caries properties when topically applied by a dentist to plaque-free teeth (although other fluorides, such stannous fluoride, are much better known for that property). However, at these levels, titanium tetrafluoride has no discernible effect in reducing the adhesion of plaque bacteria. It is an aspect of the present invention that the use of the very limited amount of titanium tetrafluoride has a plaque-reducing property which is not manifested at the higher levels of concentration. This property has not been appreciated by the art. While it is not desired to be limited to any theory of operation, it can be hypothesized that only a small amount of titanium tetrafluoride is needed to attach to protein or glycoprotein type receptor sites for titanium on plaque bacteria; such attachment to receptor sites reduces the tendency of the bacteria to adhere to teeth and to each other. However, it is further hypothesized that with larger amounts of titanium tetrafluoride, calcium fluoride is caused to form on the surface of enamel which causes an increase in adhesion of plaque. This increase in adhesion as a result of the formation of calcium fluoride severely overshadows the effect of any reduction of receptor sites. In other words, it is hypothesized that titanium tetrafluoride serves several functions, one of which has heretofore been unappreciated, namely the attachment to receptor sites on the bacteria, reducing the ability of the bacteria to adhere to each other and to tooth enamel. By limiting the amount of titanium tetrafluoride to just the amount that would be effective in attaching titanium to receptor sites but which is insufficient to cause the formation of appreciable amounts of calcium fluoride, a decrease in the adherence of plaque is obtained. Thus, the titanium tetrafluoride is used not for its caries reducing property but to reduce plaque.

The xylitol or saccharin component serves several functions. Some experiments have indicated that the combination of such compound and the small amount of titanium tetrafluoride provides a synergistic effect reducing even further the amount of plaque adhesion. Although the xylitol or saccharin serves as a sweetener, it also appears to provide an important degree of protection against bacterial adhesion to teeth and resulting caries. These compounds are somewhat unique in this regard; the use of sucrose and other such sweeteners tends to produce dextrans which can cause a rapid aggregation of plaque bacteria and which greatly increases the adhesion of plaque to teeth. This aggregation also blots out the decrease in adhesion achieved by reducing the receptor sites available. Thus, xylitol or saccharin alone decreases plaque adhesion, and in conjunction with the titanium tetrafluoride, in small concentrations, synergistically improves the reduction in plaque adhesion.

The sodium chloride is present simply to make the solution isotonic. The surfactant, for example, sodium lauryl sulfate, serves as a detergent to solubilize and emulsify plaque that is removed as a result of the cavitation procedure. Flavoring agents can be used such as peppermint, spearmint or wintergreen aromatic oils, eucalyptus oil or the like and coloring agents can be added for aesthetic purposes. A buffer can be added to maintain the desired pH generally in the range of 4.5-8.0. In this regard, the combination of sodium acetate and acetic acid can be used, as can a combination of sodium phosphate and potassium phosphate, all as known in the art. An antibacterial agent can be incorporated, such as cetylpyridinium chloride, boric acid, benzoic acid, hexylresorcinol, thymol, benzethonium chloride, or the like, as known to the art. Finally, the glycerin serves as a humectant and also serves to "smooth out" the taste of the alcohol.

The foregoing formulation can be used as a mouthwash or can be used as a coupling agent for a cavitation procedure. In cavitation, a person places a suitable amount of the liquid composition into his mouth and inserts a cavitation probe which is placed in contact with the liquid dentrifice composition and ultrasonically vibrated by means of a transducer associated with the device. Ultrasonic energy is generated and cavitation is commenced and maintained adjacent the teeth surfaces. On a daily maintenance basis, the use of the fluid results in plaque which is not as adherent as plaque which would otherwise be formed, enabling the ultrasonic probe to operate with lower power levels to remove plaque that does form. In other words, the plaque that forms is more readily removable as a result of the treatment with the dentrifice composition of the present invention. By reducing power levels the device is less likely to be instantaneously damaging and less likely to have an accumulative effect.

The present invention also has utility in topical application of hygienically clean teeth. When used by a dentist, under controlled conditions, surface absorption of titanium tetrafluoride can be effected by providing the dentrifice with a relatively high organic acid content. In this regard, the following composition will be suitable:

| Ethyl alcohol | 6-20% |
| Titanium tetrafluoride | 0.001-0.05% |
| Xylitol or saccharin | 0.5-10% (xylitol); 0.01-1.0% (saccharin) |
| Citric acid | 25-50% |
| Water | Q.S. |

Following topical application, a mouthwash formulated as first above described should be used for daily maintenance. The following examples will further illustrate the invention.

EXAMPLE 1

A liquid dentrifice can be formulated using the following components, on a weight percentage basis:

| Ethyl alcohol | 12.0% |
| Titanium tetrafluoride | 0.002% |
| Xylitol | 2.0% |
| NaCl | 0.8% |
| Sodium lauryl sulfate | 0.001% |
| Wintergreen (as flavoring agent) | 0.05% |
| FDC Blue #1, C Yellow #5 (as coloring agent) | 0.1% |
| Water | Q.S. |

The dentrifice is used by a subject who is found to have plaque on his teeth, by having the subject take a quantity of the liquid in his mouth sufficient to cover his teeth. The probe of a cavitation device, such as is illustrated in the above-referred to U.S. Pat. No. 4,236,510, is inserted through the subject's closed lips, which functions as a seal to retain the liquid. Ultrasonic energy can then be generated and cavitation commenced and maintained adjacent the teeth surfaces. The above formulation serves not only as a coupling agent but also as a means for causing plaque that remains on the teeth to become less adherent so that as the subject uses the formulation over a period of time, the plaque is more readily removed until all plaque is removed from the subject's teeth.

EXAMPLE 2

A liquid dentrifice composition for topical application of hygienically clean teeth is formulated to have the following composition on a weight percentage basis:

| Ethyl alcohol | 12.0% |
| Citric acid | 35.0% |
| Titanium tetrafluoride | 0.001% |
| Xylitol | 2.0% |
| Water | Q.S. |

A subject has his teeth hygienically cleaned to remove all plaque whereupon the solution is applied by brushing onto the teeth, maintaining the solution on the teeth for 1 to 2 minutes. Thereafter, the subject is instructed to rinse his mouth to remove the solution. Subsequently, the subject can follow the procedure of Example 1 to maintain his teeth free from plaque.

A Pit and fissure sealant, dental composite resin restoration, or a dental cement may be placed in direct contact with the tooth surface treated with the solution described in Example 2.

EXAMPLES 3 and 4

Dentifrices can be formulated as in Examples 1 and 2 but in each case substituting 0.1% saccharin for the xylitol to provide a formulation having all the described advantages.

We claim:

1. A method for reducing the adherence to teeth of plaque, comprising applying to a person's teeth a dentifrice containing 0.001–0.05% by weight titanium tetrafluoride and either at least 0.05% by weight of xylitol or at least 0.01% by weight of saccharin.

2. The method of claim 1 in which said dentrifice is in liquid form and including the step of cavitating said dental composition while it is in contact with said teeth.

3. The method of claim 2 in which said step of cavitation is accomplished by an ultrasonically vibrated probe inserted into said person's mouth and into contact with said liquid dentrifice.

4. The method of claim 1 in which said dentrifice is an aqueous alcohol solution.

5. The method of claim 4 in which said dentrifice is formulated for daily application and has the following components in percent by weight:

| | |
|---|---|
| Ethyl alcohol | 6–20% |
| Titanium tetrafluoride | 0.001–0.05% |
| Xylitol or saccharin | 0.5–10% (xylitol); 0.01–1% (saccharin) |
| NaCl | 0–4% |
| Surfactant | 0–1.0% |
| Flavoring agent | 0–5.0% |
| Coloring agent | 0–2.0% |
| Buffer | 0–1.0% |
| Antibacterial agent | 0–1.0% |
| Glycerin | 0–5.0% |
| Water | Q.S. |

6. The method of claim 4 in which said dentrifice is formulated for occassional application by a dentist and has the following components in percent by weight:

| | |
|---|---|
| Ethyl alcohol | 6–20% |
| Titanium tetrafluoride | 0.001–0.05% |
| Xylitol or saccharin | 0.5–10% (xylitol); 0.01–1% (saccharin) |
| Citric acid | 25–50% |
| Water | Q.S. |

7. A dental composition comprising a dentrifice containing 0.001–0.1% by weight of titanium tetrafluoride and 0.5–10% by weight of xylitol.

8. A dental composition comprising a dentrifice containing 0.001–0.1% by weight of titanium tetrafluoride and 0.01–1% by weight of saccharin.

9. The composition of claim 7 or 8 in which said dentrifice is an aqueous alcohol solution.

10. The composition of claim 9 having the following components in percent by weight:

| | |
|---|---|
| Ethyl alcohol | 6–20% |
| Titanium tetrafluoride | 0.001–0.05% |
| Xylitol or saccharin | 0.5–10% (xylitol); 0.01–1% (saccharin) |
| NaCl | 0–4% |
| Surfactant | 0–1% |
| Flavoring agent | 0–5% |
| Coloring agent | 0–2% |
| Buffer | 0–1% |
| Antibacterial agent | 0–1% |
| Glycerin | 0–5% |
| Water | Q.S. |

11. The composition of claim 9 having the following components in percent by weight:

| | |
|---|---|
| Ethyl alcohol | 5–20% |
| Titanium tetrafluoride | 0.001–0.05% |
| Xylitol or saccharin | 0.5–10% (xylitol); 0.01–1% (saccharin) |
| Citric acid | 25–50% |
| Water | Q.S. |

* * * * *